United States Patent [19]
Goli

[11] Patent Number: 5,958,405
[45] Date of Patent: Sep. 28, 1999

[54] HUMAN PROTEIN TYROSINE KINASE

[75] Inventor: Surya K. Goli, Sunnyvale, Calif.

[73] Assignee: Incyte Pharmaceuticals, Inc., Palo Alto, Calif.

[21] Appl. No.: 09/123,851

[22] Filed: Jul. 28, 1998

Related U.S. Application Data

[62] Division of application No. 08/728,520, Oct. 9, 1996.
[51] Int. Cl.⁶ .............................. A61K 38/46; C12N 9/12
[52] U.S. Cl. ........................................... 424/94.6; 435/194
[58] Field of Search ............................. 424/94.6; 435/194

[56] References Cited

U.S. PATENT DOCUMENTS

| | | | |
|---|---|---|---|
| 5,270,458 | 12/1993 | Lemischka | 536/23.5 |
| 5,367,057 | 11/1994 | Lemischka | 530/350 |
| 5,439,819 | 8/1995 | Littman et al. | 435/240.2 |
| 5,447,860 | 9/1995 | Ziegler | 435/240.1 |
| 5,504,000 | 4/1996 | Littman et al. | 435/194 |
| 5,573,935 | 11/1996 | Beeler et al. | 435/194 |

FOREIGN PATENT DOCUMENTS

| | | |
|---|---|---|
| 9519439 | 7/1995 | WIPO . |
| 9527060 | 10/1995 | WIPO . |

OTHER PUBLICATIONS

Charbonneau, "1002 Protein Phosphatases," *Annu. Rev. Cell Biol.*, 1992, 8:463–93.

Wilson et al., "2.2 Mb of contiguous nucleotide sequence from chromosome III of C. Elegans," *Nature*, 368:32–8 (1994) (GI 116679).

Lindberg, R.A. and T. Hunter, "cDNA Cloning and Characterization of eck, an Epithelial Cell Receptor Protein–Tyrosine Kinase in the eph/elk, Family of Protein Kinases", *Mol. Cell. Biol.*, 10: 6316–6324 (1990).

Honegger, A.M. et al., "A Mutant Epidermal Growth Factor Receptor with Defective Protein Tyrosine Kinase is Unable to Stimulate Proto–Oncogene Expression and DNA Synthesis", *Mol. Cell. Biol.*, 7: 4568–4571 (1987).

Beeler, J.F. et al., "Prokaryotic Expression Cloning of a Novel Human Tyrosine Kinase", *Mol. Cell. Biol.*, 14: 982–988 (1994).

*Primary Examiner*—Rebecca E. Prouty
*Assistant Examiner*—Einar Stole
*Attorney, Agent, or Firm*—Incyte Pharmaceuticals, Inc.

[57] ABSTRACT

The present invention provides a novel protein tyrosine kinase (HPTYK) and polynucleotides which identify and encode HPTYK. The invention also provides genetically engineered expression vectors and host cells comprising the nucleic acid sequences encoding HPTYK and a method for producing HPTYK. The invention also provides pharmaceutical compositions containing HPTYK or antagonists to HPTYK, and for the use of these compositions in the treatment of diseases associated with the expression of HPTYK. Additionally, the invention provides for the use of antisense molecules to polynucleotides encoding HPTYK for the treatment of diseases associated with the expression of HPTYK. The invention also provides diagnostic assays which utilize the polynucleotide, or fragments or the complement thereof, to hybridize to the genomic sequence or transcripts of polynucleotides encoding HPTYK or antibodies which specifically bind to HPTYK.

2 Claims, 10 Drawing Sheets

```
                                                          9                  18                 27                 36                 45                 54
5' CAG ACC TCC GCC ACA TCC TCC CTT GGT CCA GCG AGC GTT GCC GGG CCA 63                  72                 81                 90                 99                108
   GGG TCA AGC GGA GGG CTC CGA CGG CGC GGA CGG AGC GAA CGN CGA GCC ATG GCG
                                                                                                                                              M   A 117                 126                135                144                153                162
   CAC CAA ACG GGC ATC CAC GCC ACG GAG CAA GAG CTG AAG GAA TTC TTT GCC AAG GCA
    H   Q   T   G   I   H   A   T   E   E   L   K   E   F   F   A   K   A 171                 180                189                198                207                216
   CGG GCT GGC TCT GTG CGG CTC ATC AAG GTT GTG ATT GAG GAC GAN CAG CTC GTG
    R   A   G   S   V   R   L   I   K   V   V   I   E   D   X   Q   L   V 225                 234                243                252                261                270
   CTG GGT GCC TCG CAG GAG CCA TTN GGC CGC TGG CGC TGG GAT CAG GAC TAT GAC AGG GCC
    L   G   A   S   Q   E   P   X   G   R   W   D   Q   D   Y   D   R   A 279                 288                297                306                315                324
   GTG CTG CCA CTG CTG GAC GCC CAG CCC TGC TAC CTG CTC TTC CTC GAC
    V   L   P   L   L   D   A   Q   P   C   Y   L   L   F   L   D 333                 342                351                360                369                378
   TCA CAG AAT GCT CAG GGC TTC GAA TGG CTC CTC GCC TGG TCG CCT GAT AAC
    S   Q   N   A   Q   G   F   E   W   L   L   A   W   S   P   D   N
```

FIGURE 1A

```
         387       396       405       414       423       432
TCC CCC GTG CGG CTG AAG ATG CTG TAC GCG GCC ACG CGG GCC ACA GTG AAA AAG
 S   P   V   R   L   K   M   L   Y   A   A   T   R   A   T   V   K   K 441       450       459       468       477       486
GAG TTT GGA GGT GGC ATC AAG CAC ATC AAG GAT GAG CTC TTC GGG ACT GTG AAG GAT GAC
 E   F   G   G   G   H   I   K   D   E   L   F   G   T   V   K   D   D 495       504       513       522       531       540
CTC TCT TTT GCT GGG TAC CAG AAA CAC CTG TCG TCC TGT GCG GCA CCT GCC CCG
 L   S   F   A   G   Y   Q   K   H   L   S   S   C   A   A   P   A   P 549       558       567       576       585       594
CTG ACC TCG GCT GAG AGA GAG CTC CAG CAG ATC CGC ATT AAC GAG GTG AAG ACA
 L   T   S   A   E   R   E   L   Q   Q   I   R   I   N   E   V   K   T 603       612       621       630       639       648
GAG ATC AGT GTG GAA AGC AAG CAC CAG ACC CTG CAG GGC CTC GCC TTC CCC CTG
 E   I   S   V   E   S   K   H   Q   T   L   Q   G   L   A   F   P   L 657       666       675       684       693       702
CAG CCT GAG GCC CAG CGG GCA CTC CAG CAG CTC AAG CAG AAA ATG GTC AAC TAC
 Q   P   E   A   Q   R   A   L   Q   Q   L   K   Q   K   M   V   N   Y 711       720       729       738       747       756
ATC CAG ATG AAG CTG GAC CTA GAG CGG GAA ACC ATT GAG CTG GTG CAC ACA GAG
 I   Q   M   K   L   D   L   E   R   E   T   I   E   L   V   H   T   E
```

FIGURE 1B

```
      765            774            783            792            801            810
CCC ACG GAT GTG GCC CAG CTG CCC TTC CGG GTG CCC CGA GAT GCT GCC CGN TAC
 P   T   D   V   A   Q   L   P   F   R   V   P   R   D   A   A   R   Y 819            828            837            846            855            864
CAC TTN TTC CTC TAC AAG CAC AAC CAT GAG GGC GAC CCC CTT GAG TCT GTA GTG
 H   X   F   L   Y   K   H   N   H   E   G   D   P   L   E   S   V   V 873            882            891            900            909            918
TTC ATC TAC TCC ATG CCG GGG TAC AAG TGC AGC ATC AAG GAG CGA ATG CTC TAC
 F   I   Y   S   M   P   G   Y   K   C   S   I   K   E   R   M   L   Y 927            936            945            954            963            972
TCC AGC TGC AAG AGC CGC CTC CTC GAC TCC GTG GAG CAG GAC TTC CAT CTG GAG
 S   S   C   K   S   R   L   L   D   S   V   E   Q   D   F   H   L   E 981            990            999           1008           1017           1026
ATC GCC AAG AAA ATT GAG ATT GGC GAT GGG GCA GAG CTG ACG GCA GAG TTC CTC
 I   A   K   K   I   E   I   G   D   G   A   E   L   T   A   E   F   L 1035           1044           1053           1062           1071           1080
TAC GAC GAG GTG CAC CCC AAG CAA CAC GCC TTC AAG CAG GCC TTC GCC AAG CCC
 Y   D   E   V   H   P   K   Q   H   A   F   K   Q   A   F   A   K   P 1089           1098           1107           1116           1125           1134
AAG GGC CCA GGG GGC AAG CGG GGC CAT AAG CGC CTN ATC ACG CGG CCC GGG TGA
 K   G   P   G   G   K   R   G   H   K   R   L   I   T   R   P   G
```

FIGURE 1C

```
1143       1152                1161           1170            1179           1188
AAA TGG GGA TGA CAG CTA GGA GGC TGG AGC AGG GCC GGC CAC GTG TGG ACT GTG 1197       1206                1215           1224            1233           1242
GGG CTG CCC ACC TTC CGC TCC CTG CCA CCA TCC TCC TTC CTG GGC TCC AGG AAA 1251       1260                1269           1278            1287           1296
GTG TTT CTG GGA GGT CAG GAG GGC TGG CAG CTG AAC GCA CTT GCA GCG TCC GAG 1305       1314                1323           1332            1341
GGC CAC CGG GCT GGC ATT TTG TGA CCT GTT CCC TGT TGC TGT CCC TGC AT 3'
```

FIGURE 1D

| Library | Lib Description | Abun | Pct Abun |
|---|---|---|---|
| OVARTUM01 | ovarian tumor, 36 F, NORM, WM | 1 | 0.2695 |
| SYNORAT01 | synovium, elbow, rheumatoid, 51 F | 2 | 0.0955 |
| RATRNOT01 | heart, right atrium, 51 F | 1 | 0.0861 |
| OVARNOM01 | ovary, 49 F, WM | 1 | 0.0752 |
| SINTNOT02 | small intestine, 55 F | 2 | 0.0690 |
| LVENNOT03 | heart, left ventrical, 31 M | 1 | 0.0674 |
| OVARNOT02 | ovary, 59 F | 2 | 0.0630 |
| BRAINOT14 | brain, 40 F, match to BRAITUT12 | 2 | 0.0629 |
| PROSTUT01 | prostate tumor, 50 M, match to PROSNOT02 | 2 | 0.0619 |
| UTRSNOT05 | uterus, 45 F | 2 | 0.0556 |
| DUODNOT02 | small intestine, duodenum, 8 F | 2 | 0.0525 |
| BRSTNOT09 | breast, 45 F, match to BRSTTUT08 | 2 | 0.0510 |
| RATRNOT02 | heart, right atrium, 39 M | 2 | 0.0472 |
| SPLNNOT02 | spleen, 29 M | 2 | 0.0439 |
| BRAINON01 | brain, 26 M, NORM | 1 | 0.0417 |
| THP1PLB02 | THP-1 promonocyte cell line, treated PMA, LPS | 1 | 0.0407 |
| PLACNOM03 | placenta, fetal, NORM, WM | 1 | 0.0362 |
| HMC1NOT01 | HMC-1 mast cell line, 52 F | 1 | 0.0333 |
| MMLR3DT01 | macrophages (adher PBMNC), M/F, 72-hr MLR | 1 | 0.0331 |
| TBLYNOT01 | T-B lymphoblast cell line, leukemia | 1 | 0.0326 |
| LUNGFEM01 | lung, fetal, NORM, WM | 2 | 0.0296 |
| TONGTUT01 | tongue tumor, carcinoma, 36 M | 1 | 0.0295 |
| PANCTUT01 | pancreatic tumor, 65 F, match to PANCNOT08 | 1 | 0.0289 |
| THYRNOT03 | thyroid tumor, adenoma, 28 F | 2 | 0.0277 |

FIGURE 2A

| | | | |
|---|---|---|---|
| LATRTUT02 | heart tumor, myoma, 43 M | 2 | 0.0275 |
| BLADTUT05 | bladder tumor, 66 M, match to BLADNOT06 | 1 | 0.0268 |
| BRSTNOM01 | breast, F, NORM, WM | 1 | 0.0264 |
| COLNNOT23 | colon, ulcerative colitis, 16 M | 1 | 0.0264 |
| BRAITUT13 | brain tumor, meningioma, 68 M | 1 | 0.0262 |
| PANCTUT01 | pancreatic tumor, 65 F, match to PANCNOT08 | 1 | 0.0258 |
| BRSTTUT08 | breast tumor, 45 F, match to BRSTNOT09 | 1 | 0.0254 |
| TLYMNOT02 | lymphocytes (non-adher PBMNC), M/F | 2 | 0.0254 |
| UCMCL5T01 | mononuclear cells, treated IL-5 | 1 | 0.0250 |
| PROSNOT15 | prostate, 66 M, match to PROSTUT10 | 1 | 0.0241 |
| BRAINOT03 | brain, 26 M | 1 | 0.0185 |
| HNT2NOM02 | hNT2 cell line, teratocarcinoma, untreated, WM | 1 | 0.0172 |
| PGANNOT01 | paraganglionic tumor, benign paraganglioma, 46 M | 1 | 0.0160 |
| NEUTGMT01 | granulocytes, periph blood, M/F, treated GM-CSF | 1 | 0.0156 |
| BRSTNOT05 | breast, 58 F, match to BRSTTUT03 | 1 | 0.0154 |
| BRSTNOT03 | breast, 54 F, match to BRSTTUT02 | 1 | 0.0147 |
| BRAITUT01 | brain tumor, oligoastrocytoma, 50 F | 1 | 0.0134 |
| BLADTUT04 | bladder tumor, 60 M, match to BLADNOT05 | 1 | 0.0127 |
| BRAINOM01 | brain, infant F, NORM, WM | 2 | 0.0089 |

FIGURE 2B

```
  1  MAHQTGIHATEELKEFFAKARAGSVRLIKVVIEDXQLVLG  897147
  1  MSHQTGIQASEDVKEIFARARNGKYRLLKISIENEQLVIG  g451482
  1  MACQTGIRANAALRNALNLGKQAKLRLIKIVVNNEEMTPN  g1166579

41  ASQEPXGRWDQDYDRAVLPLLDAQQPCYLLYRLDSQNAQG  897147
 41  SYSQPSDSWDKDYDSFVLPLLEDKQPCYILFRLDSQNAQG  g451482
 41  YEFAGTANWRDDWRACLPDCVDAYEPCFILFRLNTIT---  g1166579

81  FEWLFLAWSPDNSPVRLKMLYAATRATVKKEFGGHIKDE   897147
 81  YEWIFIAWSPDHSHVRQKMLYAATRATLKKEFGGHIKDE   g451482
 78  -EWVLITFVDDRAPVREKMLLAATCATFKSEFGQCYIEHE  g1166579

121  LFGTVKDDLSFAGYQKHLSSCAAPAPLTSAERELQQIRIN  897147
121  VFGTVKEDVSLHGYKKYLLSQSSPAPLTAAEEELRQIKIN  g451482
117  KHVTDLKDLTLNAFEAWLKAKTELGPMSEVERELHNAQ--  g1166579

161  EVKTEISVESKHQTLQGLAFPLQPEAQRALQQLKQKMVNY  897147
161  EVQTDVGVDTKHQTLQGVAFPISREAFQALEKLNNRQLNY  g451482
155  QERAAIAHAGPQH-MKGVAFPVDRNAEEALRQLASQKLSF  g1166579

201  IQMKLDLERETIELVHT-EPTDVAQLPFRVPRDAARYHXF  897147
201  VQLEIDIKNEIIILANT-TNTELKDLPKRIPKDSARYHFF  g451482
194  VQLSVDTLNEAIKLEGTLESLEPSQLASKVPRDKPRYTFY  g1166579
```

HUMAN PROTEIN TYROSINE KINASE

This application is a divisional application of U.S. application Ser. No. 08/728,520, filed Oct. 9, 1996.

FIELD OF THE INVENTION

The present invention relates to nucleic acid and amino acid sequences of a novel human protein tyrosine kinase and to the use of these sequences in the diagnosis, study, prevention, and treatment of disease.

BACKGROUND OF THE INVENTION

Protein kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate which drives activation is generally transferred from adenosine triphosphate molecules (ATP) to a particular protein by protein kinases and removed from that protein by protein phosphatases.

Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The protein kinases comprise the largest known protein group, a superfamily of enzymes with widely varied functions and specificities. They are usually named after their substrate, their regulatory molecules, or some aspect of a mutant phenotype. Almost all kinases contain a similar 250–300 amino acid catalytic domain. The N-terminal domain, which contains subdomains I–IV, generally folds into a two-lobed structure which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes (Hardie G and Hanks S (1995) *The Protein Kinase Facts Books,* I and II, Academic Press, San Diego Calif.).

Protein tyrosine kinases, PTKs, specifically phosphorylate tyrosine residues on their target proteins and may be divided into transmembrane receptor PTKs and nontransmembrane, non-receptor PTKs. Transmembrane protein-tyrosine kinases are receptors for most growth factors. Binding of the growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Receptors that function through non-receptor PTKs include those for cytokines, hormones (growth hormone and prolactin), and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs and it is well known that cellular transformation (oncogenesis) is often accompanied by increased tyrosine phosphorylation activity (Charbonneau H and Tonks NK (1992) Annu Rev Cell Biol 8:463–93). Regulation of PTK activity may therefore be an important strategy in controlling some types of cancer.

Discovery of new human PTKs and detailed understanding of kinase pathways and signal transduction is beginning to reveal some mechanisms for interceding in the progression of inflammatory illnesses and of uncontrolled cell proliferation. The new PTK polynucleotides, polypeptides and antibodies which are the subject of this invention satisfy a need in the art in providing a plurality of tools for studying signaling cascades in various cells and tissues and for diagnosing and selecting inhibitors or drugs with the potential to intervene in various disorders or diseases in which altered kinase expression is implicated.

SUMMARY OF THE INVENTION

The present invention discloses a novel protein tyrosine kinase hereinafter referred to as HPTYK and characterized as having homology to other protein tyrosine kinases. Accordingly, the invention features substantially purified HPTYK, as shown in the amino acid sequence of SEQ ID NO:1.

One aspect of the invention features isolated and substantially purified polynucleotides which encode HPTYK. In a particular aspect, the polynucleotide is the nucleotide sequence of SEQ ID NO:2. In addition, the invention relates to polynucleotide sequences complementary to the polynucleotides encoding HPTYK, or variants thereof.

The invention further relates to the nucleic acid sequences encoding HPTYK, oligonucleotides, peptide nucleic acids, fragments, portions, or antisense molecules thereof. The present invention also relates, in part, to the inclusion of nucleic acid sequences encoding HPTYK in an expression vector which can be used to transform host cells or organisms and to a method for producing HPTYK or a fragment thereof. The invention also provides for using similar vectors for therapeutic transformation of cells to prevent proliferation of cancerous cells or tissues.

The invention contemplates the delivery of purified HPTYK or antagonists of HPTYK, alone or in a pharmaceutically acceptable excipient, to cancerous cells or tissues. It also encompasses antibodies which bind specifically to HPTYK and can be used to inhibit HPTYK and to examine prevalence of the protein in vivo.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of the novel HPTYK of the present invention. This translation was produced using MACDNASIS software (Hitachi Software Engineering Co Ltd, San Bruno Calif.).

FIGS. 2A and 2B show the northern analysis for the nucleotide sequence (SEQ ID NO:2) produced electronically using the LIFESEQ database (Incyte Pharmaceuticals, Palo Alto Calif.).

FIGS. 3A and 3B show the amino acid sequence alignments among HPTYK (SEQ ID NO:1), human PTK, A6 (GI 451482, SEQ ID NO:3; Beeler JF et al (1994) Mol Cell Biol 14 (2): 982–988) and a non-human PTK from C. elegans (GI 1166579, SEQ ID NO:4; Wilson R et al (1994) Nature 368: 32–38). Sequences were aligned using the multisequence alignment program of DNASTAR software (DNASTAR Inc., Madison Wis.).

DESCRIPTION OF THE INVENTION

Definitions

Figure 4:
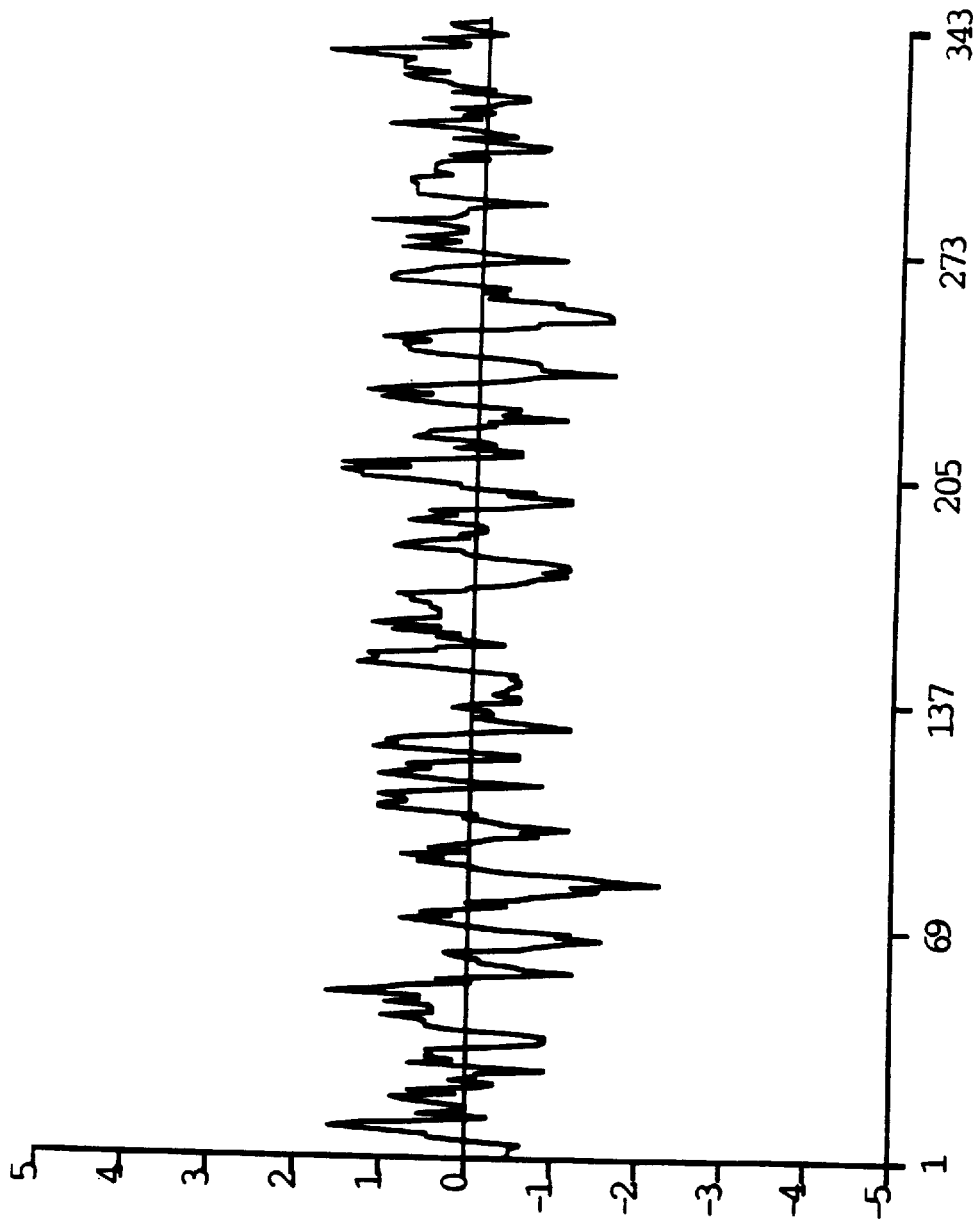
FIG. 4 shows the hydrophobicity plot for HPTYK, (SEQ ID NO:1 ) (MACDNASIS software); the X axis reflects amino acid position, and the negative Y axis reflects hydrophobicity.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Consensus" as used herein may refer to a nucleic sequence 1) which has been resequenced to resolve uncalled bases, 2) which has been extended using XL-PCR (Perkin Elmer) in the 5' and/or the 3' direction and resequenced, 3) which has been assembled from overlapping sequences of more than one Incyte alone using the GCG fragment assembly system, (GCG, Madison Wis.), or 4) which has been both extended and assembled.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring HPTYK.

A "substitution" results from the replacement of one or more nucleotides or amino acids by different nucleotides or amino acids, respectively.

As used herein, HPTYK refers to the amino acid sequence of substantially purified HPTYK obtained from any species, particularly mammalian, including bovine, ovine, porcine, murine, equine, and preferably human, from any source whether natural, synthetic, semi-synthetic or recombinant.

A "variant" of HPTYK is defined as an amino acid sequence differing by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

The term "biologically active" refers to HPTYK having structural, regulatory, or biochemical functions of a naturally occurring HPTYK. Likewise, "immunologically active" defines the capability of the natural, recombinant, or synthetic HPTYK, or any oligopeptide thereof, to induce a specific immune response in appropriate animals or cells and to bind with specific antibodies.

The term "derivative" as used herein refers to the chemical modification of a nucleic acid encoding HPTYK or the encoded HPTYK. Illustrative of such modifications would be replacement of hydrogen by an alkyl, acyl, or amino group. A nucleic acid derivative would encode a polypeptide which retains essential biological characteristics of natural HPTYK.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

The term "hybridization" as used herein shall include "any process by which a strand of nucleic acid joins with a complementary strand through base pairing" (Coombs J (1994) *Dictionary of Biotechnology,* Stockton Press, New York N.Y.). Amplification is defined as the production of additional copies of a nucleic acid sequence and is generally carried out using polymerase chain reaction technologies well known in the art (Dieffenbach C W and G S Dveksler (1995) *PCR Primer, a Laboratory Manual,* Cold Spring Harbor Press, Plainview N.Y.).

"Stringency" typically occurs in a range from about Tm-5° C. (5° C. below the melting temperature (Tm) of the probe) to about 20° C. to 25° C. below Tm. As will be understood by those of skill in the art, stringent hybridization can be used to identify or detect identical polynucleotide sequences or to identify or detect similar or related polynucleotide sequences.

Preferred Embodiments

The present invention relates to a novel human protein tyrosine kinase (HPTYK) identified among the cDNAs from a library constructed from non-cancerous breast tissue of a female diagnosed with invasive breast carcinoma, and to the use of the nucleic acid and amino acid sequences in the study, diagnosis, prevention and treatment of disease.

The nucleotide sequence, SEQ ID NO: 2, disclosed herein, was extended to full length using Incyte Clone 897147.

Figure 3B:
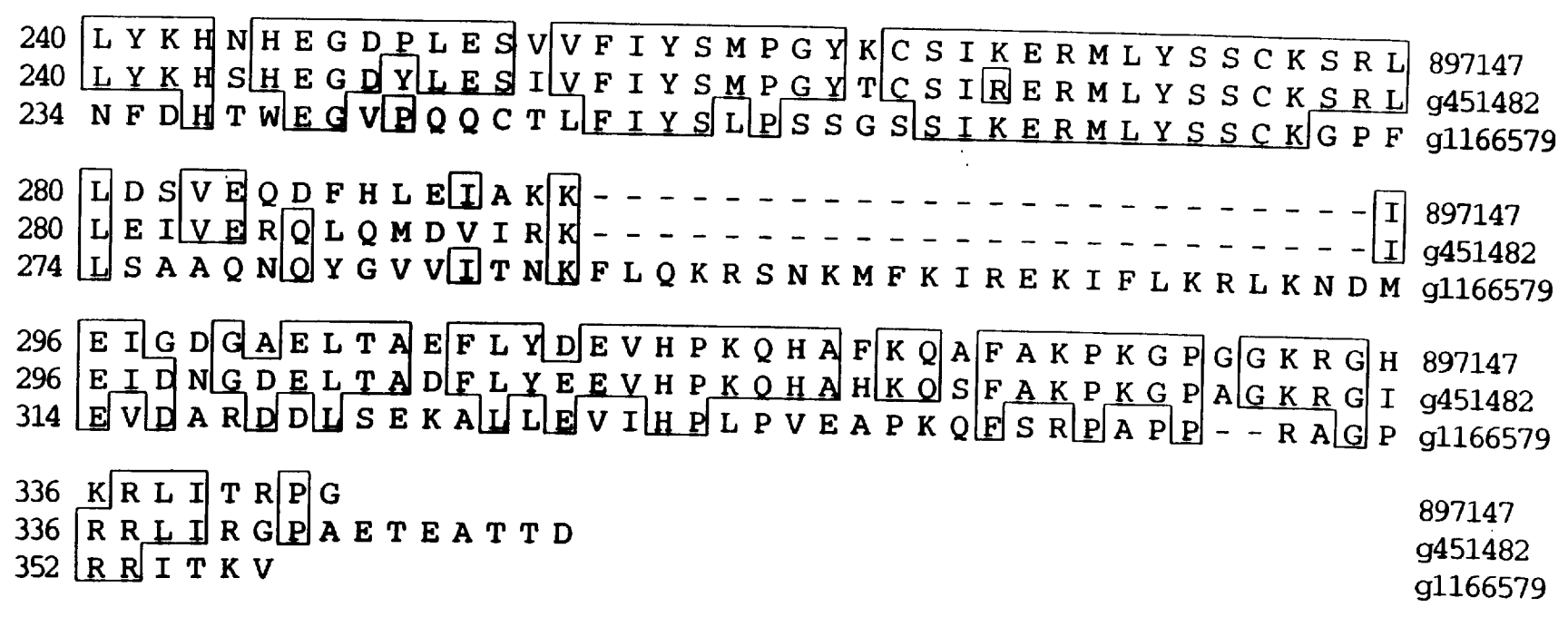

As shown in FIG. 3, cDNAs encoding portions of HPTYK were found in a variety of tumor tissues including ovarian, prostate, pancreatic, brain, bladder, breast, tongue and thyroid tumors. They were also found in various cells and tissues related to the immune system or systemic defense including macrophages, lymphocytes, and granuloycytes and associated with arthritis. It must be noted that naturally occurring expression of HPTYK is not necessarily limited to these cells and tissues.

The present invention also encompasses HPTYK variants. A preferred HPTYK variant is one having at least 80% amino acid sequence similarity to the amino acid sequence (SEQ ID NO:1), a more preferred HPTYK variant is one having at least 90% amino acid sequence similarity to SEQ ID NO:1 and a most preferred HPTYK variant is one having at least 95% amino acid sequence similarity to SEQ ID NO:1.

Figure 5:
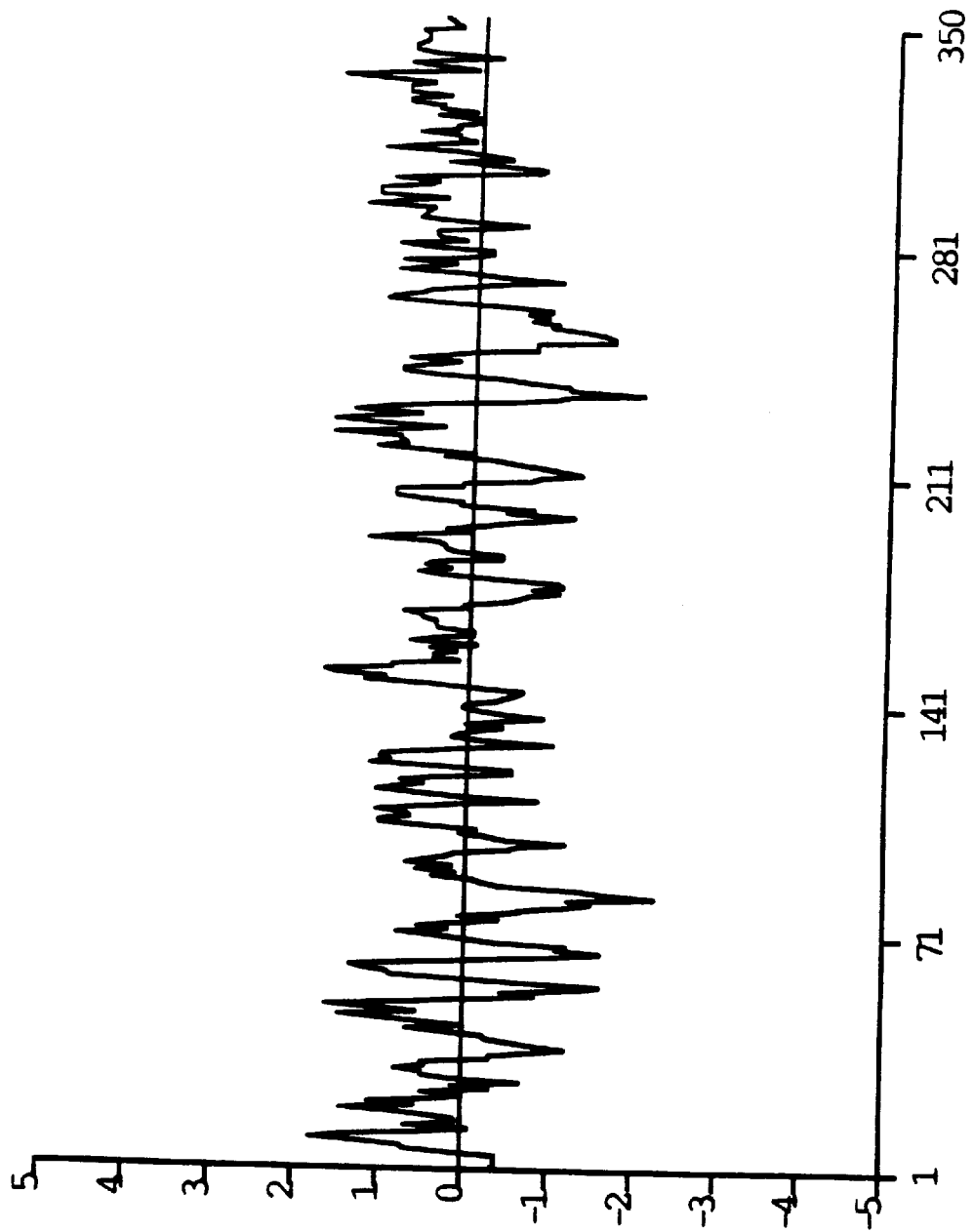
FIG. 5 shows the corresponding hydrophobicity plot for GI 451482 (SEQ ID NO:3).

Nucleic acid sequence encoding a portion of HPTYK of the present invention was first identified in cDNA, Incyte Clone 897147 (SEQ ID NO:2), through a computer-generated search for amino acid sequence alignments. The nucleic acid sequence, SEQ ID NO:2, encodes the 350 amino acid sequence of SEQ ID NO:1. The present invention is based, in part, on the chemical and structural homology among HPTYK and known PTKs from both human (GI 451482; SEQ ID NO:3) and non-human (GI 1166579; SEQ ID NO:4) sources. FIGS. 3A and 3B illustrates the sequence identities among the three molecules. GI 451482 is unusual in that, although specifically identified as a PTK by kinase assay, it does not possess any of the common sequence motifs found in the 12 subdomains of the kinase catalytic domain shared by most protein kinases (Beeler JF et al, supra). This is also true for HPTYK. Certain other characteristics of PTKs are, however, evident in these molecules. A potential N-myristolyation site (important for membrane association of non-receptor PTKs) is found at G(6) for all three molecules. Potential protein kinase C phosphorylation sites are also identified at T(107), T(124), S(265), and S(274). In addition, there are significant regions of homology between HPTYK and GI 451482 beginning at R(72), K(98), L(240), and F(307). The overall identity between these two proteins is about 65%. The hydrophobicity plots of FIGS. 4 and 5 also illustrate an overall similarity between HPTYK and GI 451482. Neither protein exhibits a significant N-terminal hydrophobic stretch characteristic of a membrane-spanning domain, and both are therefore most likely non-receptor type PTKs.

The HPTYK Coding Sequences

The extended and assembled nucleic acid and deduced amino acid sequence of HPTYK are shown in FIGS. 1A, 1B, 1C, and 1D. In accordance with the invention, any nucleic acid sequence which encodes HPTYK can be used to generate recombinant molecules which express HPTYK. In a specific embodiment described herein, a partial sequence encoding HPTYK was first isolated as Incyte Clone 897147 from a breast tissue cDNA library (BRSTNOT05).

It will be appreciated by those skilled in the art that as a result of the degeneracy of the genetic code, a multitude of HPTYK-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence encoding naturally occurring HPTYK, and all such variations are to be considered as being specifically disclosed.

Although nucleotide sequences which encode HPTYK and its variants are preferably capable of hybridizing to the nucleotide sequence of the naturally occurring sequence under appropriately selected conditions of stringency, it may be advantageous to produce nucleotide sequences encoding HPTYK or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HPTYK and its derivatives without altering the encoded amino acid sequences include the production of RNA transcripts having more desirable properties, such as a greater half-life, than transcripts produced from the naturally occurring sequence.

A DNA sequence, or portions thereof, encoding HPTYK or its derivative may be produced entirely by synthetic chemistry. After synthesis, the gene may be inserted into any of the many available DNA vectors and cell systems using reagents that are generally available. Moreover, synthetic chemistry may be used to introduce mutations into a sequence encoding HPTYK or any portion thereof.

Also included within the scope of the present invention are polynucleotide sequences that are capable of hybridizing to the nucleotide sequence of SEQ ID NO:2 under various conditions. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and on the salt concentrations under which the steps of the process are carried out.

Altered nucleic acid sequences encoding HPTYK which may be used in accordance with the invention include deletions, insertions, or substitutions of different nucleotides resulting in a polynucleotide that encodes the same or a functionally equivalent HPTYK. The protein may also show deletions, insertions, or substitutions of amino acid residues which produce a silent change and result in a functionally equivalent HPTYK. Deliberate amino acid substitutions may be made on the basis of similarity in polarity, charge, solubility, hydrophobicity, hydrophilicity, and/or the amphipathic nature of the residues as long as the biological activity of HPTYK is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles encoding HPTYK. As used herein, an "allele" or "allelic sequence" is an alternative form of the nucleic acid sequence encoding HPTYK. Alleles result from a mutation, i.e., a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions, or substitutions of amino acids. Each of these types of changes may occur alone, or in combination with the others, one or more times in a given sequence.

Methods for DNA sequencing may be used which are well known in the art and employ such enzymes as the Klenow fragment of DNA polymerase I, SEQUENASE (US Biochemical Corp, Cleveland Ohio), Taq polymerase (Perkin Elmer, Norwalk Conn.), thermostable T7 polymerase (Amersham, Chicago Ill.), or combinations of recombinant polymerases and proofreading exonucleases such as the ELONGASE amplification system marketed by Gibco BRL (Gaithersburg Md.). Preferably, the process is automated with machines such as the MICROLAB 2200 (Hamilton, Reno Nev.), Peltier thermal cycler (PTC200; MJ Research, Watertown Mass.) and the ABI 377 DNA sequencers (Perkin Elmer).

Extending the Polynucleotide Sequence

The polynucleotide sequence encoding HPTYK may be extended utilizing partial nucleotide sequence and various methods known in the art to detect upstream sequences such as promoters and regulatory elements. For example, Gobinda et al (1993; PCR Methods Applic 2:318–22) use "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO 4.05 primer analysis software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is walking PCR (Parker J D et al (1991) Nucleic Acids Res 19:3055–60), which involves targeted gene walking. Alternatively, PCR, nested primers, PROMOTOER-FINDER (Clontech, Palo Alto Calif.) and PromoterFinder libraries can be used to walk in genomic DNA. This process avoids the need to screen libraries and is useful in finding intron/exon junctions.

Preferred libraries for screening for full length cDNAs are those which have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze either the size or confirm the nucleotide sequence in sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER and SEQUENCE NAVIGATOR from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode HPTYK, fragments of the polypeptide, fusion proteins or functional equivalents thereof may be used in recombinant DNA molecules that direct the expression of HPTYK in appropriate host cells. Due to the inherent degeneracy of the genetic code, other DNA sequences which encode substantially the same or a functionally equivalent amino acid sequence, may be used to clone and express HPTYK. As will be understood by those of skill in the art, it may be advantageous to produce HPTYK-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of HPTYK expression or to produce recombinant RNA transcripts having desirable properties, such as a longer half-life, than transcripts produced from naturally occurring sequence.

The nucleotide sequences of the present invention can be engineered in order to alter HPTYK-encoding sequences for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified, or recombinant HPTYK-encoding sequence may be ligated to a heterologous sequence to encode a fusion protein. For example, for screening of peptide libraries for inhibitors of HPTYK activity, it may be useful to encode a chimeric HPTYK protein that is recognized by a commercially available antibody. A fusion protein may also be engineered to contain a cleavage site located between HPTYK and the heterologous protein sequence, so that the HPTYK may be cleaved and substantially purified away from the heterologous moiety.

In an alternate embodiment of the invention, the sequence encoding HPTYK may be synthesized, whole or in part, using chemical methods well known in the art (see Caruthers M H et al (1980) Nuc Acids Res Symp Ser 215–23, Horn T et al (1980) Nuc Acids Res Symp Ser 225–32, etc). Alternatively, the protein itself may be produced using chemical methods to synthesize an amino acid sequence for HPTYK, whole or in part. For example, peptide synthesis can be performed using various solid-phase techniques (Roberge J Y et al (1995) Science 269:202–204) and automated synthesis may be achieved, for example, using the ABI 431A peptide synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles,* W H Freeman and Co, New York N.Y.). The composition of the synthetic peptides may be confirmed by amino acid analysis or sequencing (eg, the Edman degradation procedure; Creighton, supra). Additionally the amino acid sequence of HPTYK, or any part thereof, may be altered during direct synthesis and/or combined using chemical methods with sequences from other proteins, or any part thereof, to produce a variant polypeptide.

Expression Systems

In order to express a biologically active HPTYK, the nucleotide sequence encoding HPTYK or its functional equivalent, is inserted into an appropriate expression vector, i.e., a vector which contains the necessary elements for the transcription and translation of the inserted coding sequence.

Methods which are well known to those skilled in the art can be used to construct expression vectors containing a sequence encoding HPTYK and appropriate transcriptional or translational controls. These methods include in vitro recombinant DNA techniques, synthetic techniques, and in vivo recombination or genetic recombination. Such techniques are described in Sambrook et al ((1989) *Molecular Cloning, A Laboratory Manual,* Cold Spring Harbor Press, Plainview N.Y. and Ausubel F M et al (1989) *Current Protocols in Molecular Biology,* John Wiley & Sons, New York N.Y.

A variety of expression vector/host systems may be utilized to contain and express a sequence encoding HPTYK. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUE-SCRIPT phagemid (Stratagene, LaJolla Calif.) or PSPORT1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of the sequence encoding HPTYK, vectors based on SV40 or EBV may be used with an appropriate selectable marker.

In bacterial systems, a number of expression vectors may be selected depending upon the use intended for HPTYK. For example, when large quantities of HPTYK are needed for the induction of antibodies, vectors which direct high level expression of fusion proteins that are readily purified may be desirable. Such vectors include, but are not limited to, the multifunctional *E. coli* cloning and expression vectors such as BLUESCRIPT (Stratagene), in which the sequence encoding HPTYK may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding HPTYK may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry LE McGraw Hill *Yearbook of Science and Technology* (1992) McGraw Hill New York N.Y., pp 191–196 or Weissbach and Weissbach (1988) *Methods for Plant Molecular Biology,* Academic Press, New York, N.Y., pp 421–463).

An alternative expression system which may be used to express HPTYK is an insect system. In one such system, *Autographa californica* nuclear polyhedrosis virus (AcNPV) is used as a vector to express foreign genes in *Spodoptera frugiperda* cells or in Trichoplusia larvae. The sequence encoding HPTYK may be cloned into a nonessential region of the virus, such as the polyhedrin gene, and placed under control of the polyhedrin promoter. Successful insertion of the sequence encoding HPTYK will render the polyhedrin gene inactive and produce recombinant virus lacking coat protein coat. The recombinant viruses are then used to infect *S. frugiperda* cells or Trichoplusia larvae in which HPTYK is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a sequence encoding HPTYK may be ligated into an adenovirus transcription/translation complex consisting of the late promoter and tripartite leader sequence. Insertion in a nonessential E1 or E3 region of the viral genome will result in a viable virus capable of expressing in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a sequence encoding HPTYK. These signals include the ATG initiation codon and adjacent sequences. In cases where the sequence encoding HPTYK, its initiation codon, and upstream sequences are inserted into the most appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be important for correct insertion, folding, and/or function. Different host cells such as CHO, HeLa, MDCK, 293, WI38, etc., have specific cellular machinery and characteristic mechanisms for such post-translational activities and may be chosen to ensure the correct modification and processing of the introduced foreign protein.

For long-term, high-yield production of recombinant proteins, stable expression is preferred. For example, cell lines which stably express HPTYK may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt-cells, respectively. Also, antimetabolite, antibiotic, or herbicide resistance can be used as the basis for selection; for example, dhfr, which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the sequence encoding HPTYK is inserted within a marker gene sequence, recombinant cells containing the sequence encoding HPTYK can be identified by the absence of marker gene function. Alternatively, a marker gene can be placed in tandem with the sequence encoding HPTYK under the control of a single promoter. Expression of the marker gene in response to induction or selection usually indicates expression of the tandem sequence as well.

Alternatively, host cells which contain the sequence encoding HPTYK and expressing HPTYK may be identified by a variety of procedures known to those of skill in the art. These procedures include, but are not limited to, DNA-DNA or DNA-RNA hybridization and protein bioassay or immunoassay techniques which include membrane, solution, or chip-based technologies for the detection and/or quantification of the nucleic acid or protein.

The presence of the polynucleotide sequence encoding HPTYK can be detected by DNA-DNA or DNA-RNA hybridization or amplification using probes and portions or fragments of the sequence encoding HPTYK. Nucleic acid amplification based assays involve the use of oligonucleotides or oligomers based on the nucleic acid sequence to detect transformants containing DNA or RNA encoding HPTYK. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer. A variety of protocols for detecting and measuring the expression of HPTYK, using either polyclonal or monoclonal antibodies specific for the protein, are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on HPTYK is preferred, but a competitive binding assay may be employed. These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the HPTYK-encoding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567, incorporated herein by reference.

Purification of HPTYK

Host cells transformed with a nucleotide sequence encoding HPTYK may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing sequences encoding HPTYK can be designed with signal sequences which direct secretion of HPTYK through a prokaryotic or eukaryotic cell membrane. Other recombinant constructions may join the sequence encoding HPTYK to nucleotide sequence encoding a polypeptide domain which will facilitate purification of soluble proteins (Kroll D J et al (1993) DNA Cell Biol 12:441–53; cf discussion of vectors infra containing fusion proteins).

HPTYK may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and HPTYK is useful to facilitate purification. One such expression vector provides for expression of a fusion protein comprising the sequence encoding HPTYK and nucleic acid sequence encoding 6 histidine residues followed by thioredoxin and an enterokinase cleavage site. The histidine residues facilitate purification while the enterokinase cleavage site provides a means for purifying HPTYK from the fusion protein.

In addition to recombinant production, fragments of HPTYK may be produced by direct peptide synthesis using solid-phase techniques (cf Stewart et al (1969) Solid-Phase Peptide Synthesis, W H Freeman Co, San Francisco; Merrifield J (1963) J Am Chem Soc 85:2149–2154). In vitro protein synthesis may be performed using manual techniques or by automation. Automated synthesis may be achieved, for example, using an Applied Biosystems 431A peptide synthesizer (Perkin Elmer, Foster City Calif.) in accordance with the instructions provided by the manufacturer. Various fragments of HPTYK may be chemically synthesized separately and combined using chemical methods to produce the full length molecule.

Uses of HPTYK

The rationale for the use of nucleotide and polypeptide sequences disclosed herein is based in part on the chemical and structural homology among the novel HPTYK and known PTKs. Because of the widespread roles of PTKs in growth and regulation processes in various cells and tissues, altered HPTYK expression may be implicated in a variety of disorders and diseases.

HPTYK is associated with inflammatory cells, cells of the immune system, and with various cancers. HPTYK may therefore be involved with diseases such as rheumatoid arthritis or osteoarthritis and cancers of the prostate, bladder, breast, tongue, thyroid, and brain. Alternatively, HPTYK activity may be associated with the normal cellular immune response.

Evidence has been presented of a role for overexpression of PTKs in cell transformation and cancer. Accordingly, suppression of HPTYK may be useful for treatment of various cancers, or inflammatory disease, where abnormal expression of HPTYK is involved and may be accomplished by the use of antisense molecules to HPTYK, antibodies to HPTYK, or antagonists of HPTYK. Control of HPTYK activity as a novel approach to cancer treatment may be especially useful in combination therapy with other, conventional chemotherapeutic agents. This is because 1) combinations of therapeutic agents with different cellular mechanisms of action often have synergystic effects allowing the use of lower effective doses of each agent, thus lessening the possibility of toxic side effects, and 2) combinations of different agents also lessen the possibility of developing resistance to any individual agent.

Alternatively, in cases where increased expression of HPTYK may be necessary as a part of a normal cellular immune response to a disease condition, HPTYK activity may be increased by administration of HPTYK, or by gene therapy employing sequences encoding HPTYK. Additionally, the expression of HPTYK, or parts thereof, will provide the basis for screening for agonists, antagonists or inhibitors that can be used to modulate the activity of HPTYK.

HPTYK Antibodies

HPTYK-specific antibodies are useful for the diagnosis and treatment of conditions and diseases associated with expression of HPTYK. Such antibodies include, but are not limited to, polyclonal, monoclonal, chimeric, single chain, Fab fragments, and fragments produced by a Fab expression library. Neutralizing antibodies, i.e., those which inhibit dimer formation, are especially preferred for diagnostics and therapeutics.

It is not necessary that the portion of HPTYK used for antibody induction have biological activity; however, the protein fragement, or oligopeptide must be antigenic. Peptides used to induce specific antibodies may have an amino acid sequence consisting of at least five amino acids, and preferably at least 10 amino acids. Preferably, they should mimic a portion of the amino acid sequence of the natural protein and may contain the entire amino acid sequence of a small, naturally occurring molecule. Short stretches of HPTYK amino acids may be fused with those of another protein such as keyhole limpet hemocyanin and antibody produced against the chimeric molecule. Procedures well known in the art can be used for the production of antibodies to HPTYK.

For the production of antibodies, various hosts including goats, rabbits, rats, mice, etc., may be immunized by injection with HPTYK or any portion, fragment, or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and Corynebacterium parvum are potentially useful human adjuvants.

Monoclonal antibodies to HPTYK may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030), and the EBV-hybridoma technique (Cole et al (1985) Monoclonal Antibodies and Cancer Therapy, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce HPTYK-specific single chain antibodies.

Antibodies may also be produced by inducing in vivo production in the lymphocyte population or by screening recombinant immunoglobulin libraries or panels of highly specific binding reagents, as disclosed in Orlandi et al (1989, Proc Natl Acad Sci 86: 3833–3837) and Winter G and Milstein C (1991; Nature 349:293–299).

Antibody fragments which contain specific binding sites for HPTYK may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between HPTYK and its specific antibody and the measurement of complex formation. A two-site, monoclonal-based immunoassay utilizing monoclonal antibodies reactive to two noninterfering epitopes on a specific HPTYK protein is preferred, but a competitive binding assay may also be employed. These assays are described in Maddox D E et al (1983, J Exp Med 158:1211).

Diagnostic Assays Using HPTYK Specific Antibodies

Particular HPTYK antibodies are useful for the diagnosis of conditions or diseases characterized by expression of HPTYK or in assays to monitor patients being treated with HPTYK and its fragments, agonists, or inhibitors. Diagnostic assays for HPTYK include methods utilizing the antibody and a label to detect HPTYK in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring HPTYK, using either polyclonal or monoclonal antibodies specific for the respective protein, are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HPTYK is preferred, but a competitive binding assay may be employed. These assays are described, among other places, in Maddox, D E et al (1983, J Exp Med 158:1211).

In order to provide a basis for diagnosis, normal, or standard values for HPTYK expression must be established. This is accomplished by combining body fluids or cell extracts taken from normal subjects, either animal or human, with antibody to HPTYK under conditions suitable for complex formation which are well known in the art. The amount of standard complex formation may be quantified by comparing various artificial membranes containing known quantities of HPTYK with both control and disease samples from biopsied tissues. Then, Standard values obtained from normal samples may be compared with values obtained from samples from subjects symptomatic of disease. Deviation between standard and subject values establishes the presence of a disease state.

Drug Screening

HPTYK its catalytic or immunogenic fragments or oligopeptides thereof can be used for screening therapeutic compounds in any of a variety of drug screening techniques. The fragment employed in such a test may be free in solution, affixed to a solid support, borne on a cell surface, or located intracellularly. The formation of binding complexes between HPTYK and the agent being tested may be measured.

Another technique for drug screening which may be used for high throughput screening of compounds having suitable binding affinity to the HPTYK is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of HPTYK and washed. Bound HPTYK is then detected by methods well known in the art. Substantially purified HPTYK can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HPTYK specifically compete with a test compound for binding HPTYK. In this manner, the antibodies can be used to detect the presence of any peptide which shares one or more antigenic determinants with HPTYK.

Diagnostic and Therapeutic Uses of the Polynucleotide Encoding HPTYK

A polynucleotide sequence encoding HPTYK or any part thereof may be used for diagnostic and/or therapeutic purposes. For diagnostic purposes, the sequence encoding HPTYK of this invention may be used to detect and quantitate gene expression in biopsied tissues in which HPTYK may be expressed in response to oncogenes. The diagnostic assay is useful to distinguish between absence, presence, and excess expression of HPTYK and to monitor regulation of HPTYK levels during therapeutic intervention. Included in the scope of the invention are oligonucleotide sequences, antisense RNA and DNA molecules, and peptide nucleic acids (PNA).

Another aspect of the subject invention is to provide for hybridization or PCR probes which are capable of detecting polynucleotide sequences, including genomic sequences, encoding HPTYK or closely related molecules. The specificity of the probe, whether it is made from a highly specific region, e.g., 10 unique nucleotides in the 5' regulatory region, or a less specific region, e.g., especially in the 3' region, and the stringency of the hybridization or amplification (maximal, high, intermediate, or low) will determine whether the probe identifies only naturally occurring HPTYK, alleles, or related sequences.

Probes may also be used for the detection of related sequences and should preferably contain at least 50% of the nucleotides from any of these sequences encoding HPTYK. The hybridization probes of the subject invention may be derived from the nucleotide sequence of SEQ ID NO:2 or from genomic sequence including promoter, enhancer elements, and introns of the naturally occurring sequence encoding HPTYK. Hybridization probes may be labeled by a variety of reporter groups, including radionuclides such as $^{32}$P or $^{35}$S, or enzymatic labels such as alkaline kinase coupled to the probe via avidin/biotin coupling systems, and the like.

Other means for producing specific hybridization probes for DNAs include the cloning of nucleic acid sequences encoding HPTYK or HPTYK derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Polynucleotide sequences encoding HPTYK may be used for the diagnosis of conditions or diseases with which the expression of HPTYK is associated. For example, polynucleotide sequences encoding HPTYK may be used in hybridization or PCR assays of fluids or tissues from biopsies to detect HPTYK expression. The form of such qualitative or quantitative methods may include southern or northern analysis, dot blot or other membrane-based technologies, PCR technologies and dip stick, pin, chip and ELISA technologies. All of these techniques are well known in the art and are the basis of many commercially available diagnostic kits.

The HPTYK-encoding nucleotide sequences disclosed herein provide the basis for assays that detect activation or induction of HPTYK associated with disease conditions. The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding HPTYK in the sample indicates the presence of the associated disease condition.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for HPTYK expression must be established. This is accomplished by combining body fluids or cell extracts taken from normal subjects, either animal or human, with HPTYK, or a portion thereof, under conditions suitable for hybridization or amplification. Standard hybridization may be quantified by comparing the values obtained for normal subjects with a dilution series of HPTYK run in the same experiment where a known amount of substantially purified HPTYK is used. Standard values obtained from normal samples may be compared with values obtained from samples from patients affected by HPTYK-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR may be used as described in U.S. Pat. Nos. 4,683,195 and 4,965,188 and provides additional uses for oligonucleotides based upon the sequence encoding HPTYK. Such oligomers are generally chemically synthesized, but may also be generated enzymatically or produced from a recombinant source. Oligomers generally comprise two nucleotide sequences, one with sense orientation (5'->3') and one with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radio labeling (Melby P C et al 1993 J Immunol Methods 159:235–44) or biotinylating (Duplaa C et al 1993 Anal Biochem 212:229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

As discussed previously, underexpression of HPTYK may be associated with a poor immune response to disease or, alternatively, overexpression of HPTYK may be associated with a disease condition such as inflammation or cancer. Therefore gene therapy, using a nucleotide sequence encoding HPTYK may be useful where increased HPTYK activity is needed and, conversely, an antisense molecule to a sequence encoding HPTYK may be administered where decreased expression of HPTYK is needed.

Expression vectors derived from retroviruses, adenoviruses, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense of the sequence encoding HPTYK. See, for example, the techniques described in Sambrook et al (supra) and Ausubel et al (supra).

The polynucleotides comprising full length cDNA sequences and/or its regulatory elements enable researchers to use the sequence encoding HPTYK as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding HPTYK can be turned off by transfecting a cell or tissue with expression vectors which express high levels of a desired HPTYK fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of the sequence encoding HPTYK, i.e., the promoters, enhancers, and introns. Oligonucleotides derived from the transcription initiation site, e.g., between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches,* Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding HPTYK.

Specific ribozyme cleavage sites within any potential RNA target are initially identified by scanning the target molecule for ribozyme cleavage sites which include the following sequences, GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HPTYK. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine as well as acetyl-, methyl-, thio-, and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences encoding HPTYK disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence encoding HPTYK can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques,* Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a the sequence encoding HPTYK on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of HPTYK, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio of toxic to therapeutic effects is the therapeutic index, which can be expressed as the ratio LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that HPTYK can be used to screen for therapeutic molecules which would ameliorate the adverse effects of inflammatory cells in autoimmune diseases.

The examples below are provided to illustrate the subject invention and are not included for the purpose of limiting the invention.

EXAMPLES

I BRSTNOT05 cDNA Library Construction

The BRSTNOT05 cDNA library was constructed from human breast tissue of a 58 year old Caucasian female who was diagnosed with multicentric invasive grade 4 lobular carcinoma. Tumor cells were identified in the upper outer quadrant of the left breast, forming a single predominant mass measuring 2×2×2 cm. Tumor cells were also found in the lower outer quadrant of the left breast, forming three separate nodules ranging in size from 0.3 to 0.8 cm. The surgical margins were negative for tumor, and the skin, nipple, and fascia were uninvolved. No evidence of vascular invasion was found. Eight mid and low and two high left axillary lymph nodes were negative for tumor. Prior to surgery, the patient was prescribed tamoxifen to inhibit the induction of mammary carcinoma, and she also was taking Zantac acetaminophen, and vitamin C. Previously, she was diagnosed with skin cancer, cerebrovascular disease, atherosclerosis, rheumatic heart disease, and osteoarthritis. The family history included breast cancer in the mother and prostate cancer in a brother. BRSTTUT03 is a breast tumor library from the same donor.

The excised tissue was frozen, homogenized, and lysed using a Polytron PT-3000 homogenizer (Brinkmann Instruments, Westbury N.J.) in guanidinium isothiocyanate solution. The lysate was centrifuged over a 5.7M CsCl cushion using an SW28 rotor in an L8-70M ultracentrifuge (Beckman Instruments) for 18 hours at 25,000 rpm at ambient temperature. The RNA was extracted with acid phenol pH 4.0, precipitated using 0.3M sodium acetate and 2.5 volumes of ethanol, resuspended in RNAse-free water and DNase treated at 37° C. The RNA extraction was repeated with acid phenol chloroform pH 8.0 and precipitated with sodium acetate and ethanol as before. The mRNA was then isolated using the OLIGOTEX kit (QIAGEN Inc.; Chatsworth Calif.) and used to construct the cDNA library.

The mRNA was handled according to the recommended protocols in the SUPERSCRIPT plasmid system for cDNA synthesis and plasmid cloning (Cat. #18248-013; Gibco/BRL), cDNAs were fractionated on a SEPHAROSE CL4B column (Cat. #275105-01; Pharmacia), and those cDNAs exceeding 400 bp were ligated into PSPORT1. The plasmid PSPORT1 was subsequently transformed into DH5α competent cells (Cat. #18258-012; Gibco/BRL).

II Isolation and Sequencing of cDNA Clones

Plasmid DNA was released from the cells and purified using the R.E.A.L. Prep 96 plasmid kit for rapid extraction alkaline lysis plasmid minipreps (Catalog #26173; QIAGEN, Inc.). This kit enables the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger F and A R Coulson (1975; J Mol Biol 94:441f), using a MICROLAB 2200 (Hamilton, Reno Nev.) in combination with Peltier thermal cyclers (PTC200 from MJ Research, Watertown Mass.), and Applied Biosystems 377 DNA sequencing systems; and the reading frame was determined.

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 sequence analysis system in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques using BLAST (Altschul S F 1993 and 1990, supra) are used to search for identical or related molecules in nucleotide databases such as the GenBank or the LIFESEQ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

% sequence identity×% maximum BLAST score/100 and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of the search shown in FIGS. 2A and 2B are reported as a list of libraries in which the HPTYK encoding sequence occurs. Abundance and percentage abundance of the HPTYK encoding sequence are also reported. Abundance directly reflects the number of times a particular transcript is represented in a cDNA library, and percent abundance is abundance divided by the total number of sequences examined in the cDNA library.

V Extension of the Sequence Encoding HPTYK

The nucleic acid sequence of SEQ ID No:2 is used to design oligo-nucleotide primers for extending a partial nucleotide sequence to full length or for obtaining 5' sequence from genomic libraries. One primer is synthesized to initiate extension in the antisense direction (XLR) and the other is synthesized to extend sequence in the sense direction (XLF). Primers allow the extension of the known sequence "outward" generating amplicons containing new, unknown nucleotide sequences for the region of interest (U.S. patent application Ser. No. 08/487,112, filed Jun. 7, 1995, specifically incorporated by reference). The initial primers are designed from the cDNA using OLIGO 4.06 primer analysis software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library, are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; M J Research, Watertown Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 ml aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 ml of ligation buffer, 1 ml T4-DNA ligase (15 units) and 1 ml T4 polynucleotide kinase are added, and the mixture is incubated at room temperature for 2–3 hours or overnight at 16° C. Competent E coli cells (in 40 ml of appropriate media) are transformed with 3 ml of ligation mixture and cultured in 80 ml of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 ml of liquid LB/2×Carb medium placed in an individual well of an appropriate, commercially-available, sterile 96-well microtiter plate. The following day, 5 ml of each overnight culture is transferred into a non-sterile 96-well plate and after dilution 1:10 with water, 5 ml of each sample is transferred into a PCR array.

For PCR amplification, 18 ml of concentrated PCR reaction mix (3.3×) containing 4 units of rTth DNA polymerase, a vector primer and one or both of the gene specific primers used for the extension reaction are added to each well. Amplification is performed using the following conditions:

Step 1 94° C. for 60 sec

Step 2 94° C. for 20 sec

Step 3 55° C. for 30 sec

Step 4 72° C. for 90 sec

Step 5 Repeat steps 2–4 for an additional 29 cycles

Step 6 72° C. for 180 sec

Step 7 4° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID No:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 mCi of [-$^{32}$P] adenosine triphosphate (Amersham, Chicago Ill.) and T4 polynucleotide kinase (DuPont NEN, Boston Mass.). The labeled oligonucleotides are substantially purified with SEPHADEX G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (NYTRAN Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Kodak, Rochester N.Y.) is exposed to the blots or the blots are exposed in a Phosphoimager cassette (Molecular Dynamics, Sunnyvale Calif.), hybridization patterns are compared visually.

VII Antisense Molecules

The sequence encoding HPTYK, or any part thereof, is used to inhibit in vivo or in vitro expression of naturally occurring sequence. Although use of antisense oligonucleotides, comprising about 20 base-pairs, is specifically described, essentially the same procedure is used with larger cDNA fragments. An oligonucleotide complementary to a portion of the coding sequence of HPTYK as shown in SEQ ID No:2 is used to inhibit expression of the naturally occurring sequence. The complementary oligonucleotide is designed from the most unique 5' sequence and used either to inhibit transcription by preventing promoter binding to the upstream nontranslated sequence or translation of a transcript encoding HPTYK by preventing the ribosome from binding. Using an appropriate portion of the leader and 5' sequence of SEQ ID No:2 an effective antisense oligonucleotide includes any 15–20 nucleotides spanning the region which translates into the signal or early coding sequence of the polypeptide as shown in FIGS. 1A, 1B, 1C, and 1D.

VIII Expression of HPTYK

Expression of HPTYK is accomplished by subcloning the cDNAs into appropriate vectors and transfecting the vectors into host cells. In this case, the cloning vector, pSport, previously used for the generation of the cDNA library is used to express HPTYK in E. coli. Upstream of the cloning site, this vector contains a promoter for β-galactosidase, followed by sequences containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length HPTYK. The signal sequence directs the secretion of HPTYK into the bacterial growth media which can be used directly in the following assay for activity.

IX Assay for HPTYK Activity

HPTYK activity may be measured by phosphorylation of a protein substrate such as myelin basic protein using gamma-labeled $^{32}$P-ATP and quantitation of the incorporated radioactivity using a gamma radioisotope counter. HPTYK is incubated with the protein substrate, $^{32}$P-ATP, and a kinase buffer. The $^{32}$P incorporated into the substrate is then separated from free $^{32}$P-ATP by electrophoresis and the incorporated $^{32}$P is counted. A determination of the specific amino acid residues phosphorylated is made by phosphoamino acid analysis of the hydrolyzed protein as described by Boyle W J et al (1991) Methods in Enzymol 201: 110–148.

X Production of HPTYX Specific Antibodies

HPTYK is substantially purified using PAGE electrophoresis (Sambrook, supra) is used to immunize rabbits and to produce antibodies using standard protocols. The amino acid sequence translated from HPTYK is analyzed using DNASTAR software (DNASTAR Inc) to determine regions of high immunogenicity and a corresponding oligopeptide is synthesized and used to raise antibodies by means known to those of skill in the art. Analysis to select appropriate epitopes, such as those near the C-terminus or in hydrophilic regions is described by Ausubel F M et al (supra).

Typically, the oligopeptides are 15 residues in length, synthesized using an Applied Biosystems 431A synthesizer model using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HPTYK Using Specific Antibodies

Naturally occurring or recombinant HPTYK is substantially purified by immunoaffinity chromatography using antibodies specific for HPTYK. An immunoaffinity column is constructed by covalently coupling HPTYK antibody to an activated chromatographic resin such as CnBr-activated SEPHAROSE (Pharmacia Biotech). After the coupling, the resin is blocked and washed according to the manufacturer's instructions.

Media containing HPTYK is passed over the immunoaffinity column, and the column is washed under conditions that allow the preferential absorbance of HPTYK (eg, high ionic strength buffers in the presence of detergent). The column is eluted under conditions that disrupt antibody/HPTYK binding (eg, a buffer of pH 2–3 or a high concentration of a chaotrope such as urea or thiocyanate ion), and HPTYK is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A substantially purified human protein tyrosine kinase polypeptide comprising the amino acid sequence of SEQ ID NO:1 or enzymatically active fragments thereof.

2. A pharmaceutical composition comprising a substantially purified human protein tyrosine kinase polypeptide having the amino acid sequence of SEQ ID NO: 1 or enzymatically active fragments thereof in conjunction with a suitable pharmaceutical carrier.

* * * * *

```
                              SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
          (A) LENGTH: 343 amino acids
          (B) TYPE: amino acid
          (C) STRANDEDNESS: single
          (D) TOPOLOGY: linear (ii) MOLECULE TYPE: peptide (vii) IMMEDIATE SOURCE:
          (A) LIBRARY:
          (B) CLONE: Consensus (xi) SEQUENCE DESCRIPTION: SEQ ID NO:1:

Met Ala His Gln Thr Gly Ile His Ala Thr Glu Glu Leu Lys Glu Phe
 1               5                  10                  15

Phe Ala Lys Ala Arg Ala Gly Ser Val Arg Leu Ile Lys Val Val Ile
            20                  25                  30

Glu Asp Xaa Gln Leu Val Leu Gly Ala Ser Gln Glu Pro Xaa Gly Arg
        35                  40                  45

Trp Asp Gln Asp Tyr Asp Arg Ala Val Leu Pro Leu Leu Asp Ala Gln
    50                  55                  60

Gln Pro Cys Tyr Leu Leu Tyr Arg Leu Asp Ser Gln Asn Ala Gln Gly
65                  70                  75                  80

Phe Glu Trp Leu Phe Leu Ala Trp Ser Pro Asp Asn Ser Pro Val Arg
                85                  90                  95

Leu Lys Met Leu Tyr Ala Ala Thr Arg Ala Thr Val Lys Lys Glu Phe
            100                 105                 110

Gly Gly Gly His Ile Lys Asp Glu Leu Phe Gly Thr Val Lys Asp Asp
```

```
                    115                 120                 125
Leu Ser Phe Ala Gly Tyr Gln Lys His Leu Ser Ser Cys Ala Ala Pro
    130                 135                 140

Ala Pro Leu Thr Ser Ala Glu Arg Glu Leu Gln Gln Ile Arg Ile Asn
145                 150                 155                 160

Glu Val Lys Thr Glu Ile Ser Val Glu Ser Lys His Gln Thr Leu Gln
                165                 170                 175

Gly Leu Ala Phe Pro Leu Gln Pro Glu Ala Gln Arg Ala Leu Gln Gln
            180                 185                 190

Leu Lys Gln Lys Met Val Asn Tyr Ile Gln Met Lys Leu Asp Leu Glu
    195                 200                 205

Arg Glu Thr Ile Glu Leu Val His Thr Glu Pro Thr Asp Val Ala Gln
    210                 215                 220

Leu Pro Phe Arg Val Pro Arg Asp Ala Ala Arg Tyr His Xaa Phe Leu
225                 230                 235                 240

Tyr Lys His Asn His Glu Gly Asp Pro Leu Glu Ser Val Val Phe Ile
                245                 250                 255

Tyr Ser Met Pro Gly Tyr Lys Cys Ser Ile Lys Glu Arg Met Leu Tyr
            260                 265                 270

Ser Ser Cys Lys Ser Arg Leu Leu Asp Ser Val Glu Gln Asp Phe His
    275                 280                 285

Leu Glu Ile Ala Lys Lys Ile Glu Ile Gly Asp Gly Ala Glu Leu Thr
    290                 295                 300

Ala Glu Phe Leu Tyr Asp Glu Val His Pro Lys Gln His Ala Phe Lys
305                 310                 315                 320

Gln Ala Phe Ala Lys Pro Lys Gly Pro Gly Gly Lys Arg Gly His Lys
                325                 330                 335

Arg Leu Ile Thr Arg Pro Gly
            340

(2) INFORMATION FOR SEQ ID NO:2:

(i) SEQUENCE CHARACTERISTICS:
         (A) LENGTH: 1346 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (A) LIBRARY:
         (B) CLONE: Consensus (xi) SEQUENCE DESCRIPTION: SEQ ID NO:2:

CAGACCTCCG CCACATCCTC CACCTCTCTT GGTCCAGCGA GCGTTGCCGG GCCAGGGTCA    60

AGCGGAGGGC TCCGACGGCG CGGACGGAGC GAACGNCGAG CCATGGCGCA CCAAACGGGC   120

ATCCACGCCA GGAAGAGCT GAAGGAATTC TTTGCCAAGG CACGGGCTGG CTCTGTGCGG    180

CTCATCAAGG TTGTGATTGA GGACGANCAG CTCGTGCTGG GTGCCTCGCA GGAGCCATTN   240

GGCCGCTGGG ATCAGGACTA TGACAGGGCC GTGCTGCCAC TGCTGGACGC CCAGCAGCCC   300

TGCTACCTGC TCTACCGCCT CGACTCACAG AATGCTCAGG CTTCGAATG GCTCTTCCTC    360

GCCTGGTCGC CTGATAACTC CCCCGTGCGG CTGAAGATGC TGTACGCGGC CACGCGGGCC   420

ACAGTGAAAA AGGAGTTTGG AGGTGGCCAC ATCAAGGATG AGCTCTTCGG GACTGTGAAG   480

GATGACCTCT CTTTTGCTGG GTACCAGAAA CACCTGTCGT CCTGTGCGGC ACCTGCCCCG   540

CTGACCTCGG CTGAGAGAGA GCTCCAGCAG ATCCGCATTA ACGAGGTGAA GACAGAGATC   600
```

```
AGTGTGGAAA GCAAGCACCA GACCCTGCAG GGCCTCGCCT TCCCCCTGCA GCCTGAGGCC     660

CAGCGGGCAC TCCAGCAGCT CAAGCAGAAA ATGGTCAACT ACATCCAGAT GAAGCTGGAC     720

CTAGAGCGGG AAACCATTGA GCTGGTGCAC ACAGAGCCCA CGGATGTGGC CCAGCTGCCC     780

TTCCGGGTGC CCCGAGATGC TGCCCGNTAC CACTTNTTCC TCTACAAGCA CAACCATGAG     840

GGCGACCCCC TTGAGTCTGT AGTGTTCATC TACTCCATGC CGGGGTACAA GTGCAGCATC     900

AAGGAGCGAA TGCTCTACTC CAGCTGCAAG AGCCGCCTCC TCGACTCCGT GGAGCAGGAC     960

TTCCATCTGG AGATCGCCAA GAAAATTGAG ATTGGCGATG GGCAGAGCT GACGGCAGAG    1020

TTCCTCTACG ACGAGGTGCA CCCCAAGCAA CACGCCTTCA GCAGGCCTT CGCCAAGCCC    1080

AAGGGCCCAG GGGGCAAGCG GGGCCATAAG CGCCTNATCA CGCGGCCCGG GTGAAAATGG    1140

GGATGACAGC TAGGAGGCTG GAGCAGGGCC GGCCACGTGT GGACTGTGGG GCTGCCCACC    1200

TTCCGCTCCC TGCCACCATC CTCCTTCCTG GGCTCCAGGA AAGTGTTTCT GGGAGGTCAG    1260

GAGGGCTGGC AGCTGAACGC ACTTGCAGCG TCCGAGGGCC ACCGGGCTGG CATTTTGTGA    1320

CCTGTTCCCT GTTGCTGTCC CTGCAT                                        1346
```

(2) INFORMATION FOR SEQ ID NO:3:

(i) SEQUENCE CHARACTERISTICS:
        (A) LENGTH: 350 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 451482

(xi) SEQUENCE DESCRIPTION: SEQ ID NO:3:

```
Met Ser His Gln Thr Gly Ile Gln Ala Ser Glu Asp Val Lys Glu Ile
  1               5                  10                  15

Phe Ala Arg Ala Arg Asn Gly Lys Tyr Arg Leu Leu Lys Ile Ser Ile
             20                  25                  30

Glu Asn Glu Gln Leu Val Ile Gly Ser Tyr Ser Gln Pro Ser Asp Ser
         35                  40                  45

Trp Asp Lys Asp Tyr Asp Ser Phe Val Leu Pro Leu Leu Glu Asp Lys
     50                  55                  60

Gln Pro Cys Tyr Ile Leu Phe Arg Leu Asp Ser Gln Asn Ala Gln Gly
 65                  70                  75                  80

Tyr Glu Trp Ile Phe Ile Ala Trp Ser Pro Asp His Ser His Val Arg
                 85                  90                  95

Gln Lys Met Leu Tyr Ala Ala Thr Arg Ala Thr Leu Lys Lys Glu Phe
            100                 105                 110

Gly Gly Gly His Ile Lys Asp Glu Val Phe Gly Thr Val Lys Glu Asp
        115                 120                 125

Val Ser Leu His Gly Tyr Lys Lys Tyr Leu Leu Ser Gln Ser Ser Pro
    130                 135                 140

Ala Pro Leu Thr Ala Ala Glu Glu Leu Arg Gln Ile Lys Ile Asn
145                 150                 155                 160

Glu Val Gln Thr Asp Val Gly Val Asp Thr Lys His Gln Thr Leu Gln
                165                 170                 175

Gly Val Ala Phe Pro Ile Ser Arg Glu Ala Phe Gln Ala Leu Glu Lys
            180                 185                 190
```

-continued

```
Leu Asn Asn Arg Gln Leu Asn Tyr Val Gln Leu Glu Ile Asp Ile Lys
    195                 200                 205

Asn Glu Ile Ile Ile Leu Ala Asn Thr Thr Asn Thr Glu Leu Lys Asp
210                 215                 220

Leu Pro Lys Arg Ile Pro Lys Asp Ser Ala Arg Tyr His Phe Phe Leu
225                 230                 235                 240

Tyr Lys His Ser His Glu Gly Asp Tyr Leu Glu Ser Ile Val Phe Ile
                245                 250                 255

Tyr Ser Met Pro Gly Tyr Thr Cys Ser Ile Arg Glu Arg Met Leu Tyr
            260                 265                 270

Ser Ser Cys Lys Ser Arg Leu Leu Glu Ile Val Glu Arg Gln Leu Gln
        275                 280                 285

Met Asp Val Ile Arg Lys Ile Glu Ile Asp Asn Gly Asp Glu Leu Thr
290                 295                 300

Ala Asp Phe Leu Tyr Glu Glu Val His Pro Lys Gln His Ala His Lys
305                 310                 315                 320

Gln Ser Phe Ala Lys Pro Lys Gly Pro Ala Gly Lys Arg Gly Ile Arg
                325                 330                 335

Arg Leu Ile Arg Gly Pro Ala Glu Thr Glu Ala Thr Thr Asp
            340                 345                 350

(2) INFORMATION FOR SEQ ID NO:4:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1166579

(xi) SEQUENCE DESCRIPTION: SEQ ID NO:4:

Met Ala Cys Gln Thr Gly Ile Arg Ala Asn Ala Ala Leu Arg Asn Ala
1               5                   10                  15

Leu Asn Leu Gly Lys Gln Ala Lys Leu Arg Leu Ile Lys Ile Val Val
                20                  25                  30

Asn Asn Glu Glu Met Thr Pro Asn Tyr Glu Phe Ala Gly Thr Ala Asn
            35                  40                  45

Trp Arg Asp Asp Trp Arg Ala Cys Leu Pro Asp Cys Val Asp Ala Tyr
        50                  55                  60

Glu Pro Cys Phe Ile Leu Phe Arg Leu Asn Thr Ile Thr Glu Trp Val
65                  70                  75                  80

Leu Ile Thr Phe Val Asp Asp Arg Ala Pro Val Arg Glu Lys Met Leu
                85                  90                  95

Leu Ala Ala Thr Cys Ala Thr Phe Lys Ser Glu Phe Gly Gln Cys Tyr
            100                 105                 110

Ile Glu His Glu Lys His Val Thr Asp Leu Lys Asp Leu Thr Leu Asn
        115                 120                 125

Ala Phe Glu Ala Trp Leu Lys Ala Lys Thr Glu Leu Gly Pro Met Ser
130                 135                 140

Glu Val Glu Arg Glu Leu His Asn Ala Gln Gln Glu Arg Ala Ala Ile
145                 150                 155                 160

Ala His Ala Gly Pro Gln His Met Lys Gly Val Ala Phe Pro Val Asp
                165                 170                 175
```

```
Arg Asn Ala Glu Glu Ala Leu Arg Gln Leu Ala Ser Gln Lys Leu Ser
            180                 185                 190

Phe Val Gln Leu Ser Val Asp Thr Leu Asn Glu Ala Ile Lys Leu Glu
            195                 200                 205

Gly Thr Leu Glu Ser Leu Glu Pro Ser Gln Leu Ala Ser Lys Val Pro
            210                 215                 220

Arg Asp Lys Pro Arg Tyr Thr Phe Tyr Asn Phe Asp His Thr Trp Glu
225                 230                 235                 240

Gly Val Pro Gln Gln Cys Thr Leu Phe Ile Tyr Ser Leu Pro Ser Ser
            245                 250                 255

Gly Ser Ser Ile Lys Glu Arg Met Leu Tyr Ser Ser Cys Lys Gly Pro
            260                 265                 270

Phe Leu Ser Ala Ala Gln Asn Gln Tyr Gly Val Val Ile Thr Asn Lys
            275                 280                 285

Phe Leu Gln Lys Arg Ser Asn Lys Met Phe Lys Ile Arg Glu Lys Ile
            290                 295                 300

Phe Leu Lys Arg Leu Lys Asn Asp Met Glu Val Asp Ala Arg Asp Asp
305                 310                 315                 320

Leu Ser Glu Lys Ala Leu Leu Glu Val Ile His Pro Leu Pro Val Glu
            325                 330                 335

Ala Pro Lys Gln Phe Ser Arg Pro Ala Pro Pro Arg Ala Gly Pro Arg
            340                 345                 350

Arg Ile Thr Lys Val
            355
```